United States Patent
van der Berge et al.

(10) Patent No.: US 6,812,181 B2
(45) Date of Patent: Nov. 2, 2004

(54) COATED ZEOLITE CATALYSTS AND USE FOR HYDROCARBON CONVERSION

(75) Inventors: Jannetje Maatje van der Berge, Oostvoorne (NL); Gary David Mohr, League City, TX (US); Kenneth Ray Clem, Humble, TX (US); Wilfried Jozef Mortier, Kessel-lo (BE); Machteld Maria Mertens, Boortmeerbeek (BE); Michael C. Bradford, Waltham, MA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 10/309,453

(22) Filed: Dec. 4, 2002

(65) Prior Publication Data

US 2003/0121827 A1 Jul. 3, 2003

Related U.S. Application Data

(62) Division of application No. 09/204,576, filed on Dec. 3, 1998, now Pat. No. 6,504,074.
(60) Provisional application No. 60/067,415, filed on Dec. 3, 1997.

(51) Int. Cl.[7] .............................................. B01J 29/06
(52) U.S. Cl. ............................. 502/67; 502/61; 502/64; 502/78; 502/69
(58) Field of Search ............................ 502/67, 61, 64, 502/78, 69

(56) References Cited

U.S. PATENT DOCUMENTS

| | | | |
|---|---|---|---|
| 3,730,910 A | 5/1973 | Albers et al. | 252/455 Z |
| 4,097,543 A | 6/1978 | Haag et al. | 260/672 T |
| 4,482,774 A | 11/1984 | Koetsier | 585/481 |
| 4,946,580 A | 8/1990 | Fajula et al. | 208/120 |
| 5,525,563 A | 6/1996 | Thiele et al. | 502/69 |
| 5,665,325 A | 9/1997 | Verduijn | 423/709 |
| 6,699,811 B1 * | 3/2004 | Mohr et al. | 502/67 |

FOREIGN PATENT DOCUMENTS

| | | | |
|---|---|---|---|
| EP | 0118632 | 9/1984 | C01B/33/28 |
| EP | 0251892 | 1/1988 | B01J/29/06 |
| EP | 0599117 | 6/1994 | B01J/29/06 |
| JP | 59-16832 | 1/1984 | |
| WO | WO97/03019 | 4/1993 | C01B/33/334 |
| WO | WO94/05597 | 3/1994 | C01B/33/26 |
| WO | WO96/16004 | 5/1996 | C07C/2/66 |
| WO | WO96/24567 | 8/1996 | C07C/2/12 |
| WO | WO97/45197 | 12/1997 | B01J/29/06 |
| WO | WO97/45386 | 12/1997 | C07C/15/00 |
| WO | WO97/45387 | 12/1997 | C07C/12/08 |

* cited by examiner

*Primary Examiner*—Kiley Stoner
*Assistant Examiner*—Christina Ildebrando (57) ABSTRACT

There is provided a coated zeolite catalyst in which the accessibility of the acid sites on the external surfaces of the zeolite is controlled and a process for converting hydrocarbons utilizing the coated zeolite catalyst. The zeolite catalyst comprises core crystals of a first zeolite and a discontinuous layer of smaller size second crystals of a second zeolite which cover at least a portion of the external surface of the first crystals The coated zeolite catalyst finds particular application in hydrocarbon conversion processes where catalyst activity in combination with zeolite structure are important for reaction selectivity, e.g., catalytic cracking, alkylation, disproportional of toluene, isomerization, and transalkylation reactions.

27 Claims, 2 Drawing Sheets

COATED ZEOLITE CATALYSTS AND USE FOR HYDROCARBON CONVERSION

This application is a divisional of U.S. application Ser. No. 09/204,576, filed Dec. 3, 1998, now U.S. Pat. No. 6,504,074, which claims priority to U.S. Provisional Application No. 60/067,415, filed Dec. 3, 1997.

FIELD OF THE INVENTION

This invention relates to coated zeolite catalysts having controlled external surface acidity and the use of the coated zeolite catalysts in hydrocarbon conversion processes.

BACKGROUND OF THE INVENTION

Crystalline microporous molecular sieves, both natural and synthetic, have been demonstrated to have catalytic properties for various types of hydrocarbon conversion processes. In addition, the crystalline microporous molecular sieves have been used as adsorbents and catalyst carriers for various types of hydrocarbon conversion processes, and other applications. These molecular sieves are ordered, porous, crystalline material having a definite crystalline structure as determined by x-ray diffraction, within which there are a large number of smaller cavities which may be interconnected by a number of still smaller channels or pores. The dimensions of these channels or pores are such as to allow for adsorption of molecules with certain dimensions while rejecting those of large dimensions. The interstitial spaces or channels formed by the crystalline network enable molecular sieves such as crystalline silicates, aluminosilicates, crystalline silicoalumino phosphates, and crystalline aluminophosphates, to be used as molecular sieves in separation processes and catalysts and catalyst supports in a wide variety of hydrocarbon conversion processes.

Zeolites are comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as gallosilicates, silicoaluminophosphates (SAPO) and aluminophosphates (ALPO). The term "aluminosilicate zeolite", as used herein, shall mean zeolite materials consisting essentially of silicon and aluminum atoms in the crystalline lattice structure thereof Within a pore of the zeolite, hydrocarbon conversion reactions such as paraffin isomerization, olefin skeletal or double bond isomerization, disproportionation, alkylation, and transalkylation of aromatics are governed by constraints imposed by the channel size of the zeolite. Reactant selectivity occurs when a fraction of the feedstock is too large to enter the pores to react; while product selectivity occurs when some of the products can not leave the channels or do not subsequently react. Product distributions can also be altered by transition state selectivity in which certain reactions can not occur because the reaction transition state is too large to form within the pores. Shape selectivity can also result from configuration constraints on diffusion where the dimensions of the molecule approach that of the pore.

Non-selective reactions on the external surface acid sites of zeolites are usually not desirable because they are not subject to the shape selective constraints imposed on those reactions occurring within the channels of the zeolites and are often not desirable. For example, the surface acid sites can adversely effect reactants entering the pores of the zeolite and products exiting the pores of the zeolite.

Various procedures have been prepared for limiting surface acidity of the zeolites. For example, the surface acidity of aluminosilicate zeolites can be reduced by dealumination of the zeolite surface. Techniques for the dealumination include hydrothermal treatment, mineral acid treatment with HCl, $HNO_3$, or $H_2SO_4$, and chemical treatment with $SiCl_4$ and EDTA. A problem associated with these procedures is that they can degrade the zeolite crystals and/or cause the zeolite crystals to lose sorption capacity. Still further, dealumination can also reduce the overall activity of the zeolite, which can result in reduced catalyst activity and/or activity maintenance.

Another procedure for limiting the surface acidity of zeolites, as disclosed in U.S. Pat. No. 4,203,869, involves synthesizing an isocrystalline layer of aluminum-free zeolite over the surface of the zeolite.

The present invention is directed to coated zeolite catalysts and the use of the coated zeolite catalysts in hydrocarbon conversion processes.

SUMMARY OF THE INVENTION

In accordance with the present invention, there are provided zeolite catalysts having an external surface zeolite coating. The coated zeolite catalysts comprise first crystals of a first zeolite and smaller size second crystals of a second zeolite. The smaller size second crystals provide a coating on at least a portion of the external surface of the first crystals.

The coated zeolite catalysts of the present invention have enhanced performance when utilized in hydrocarbon conversion processes. The coated zeolite catalysts of the present invention finds particular application in hydrocarbon conversion processes where catalyst acidity in combination with zeolite structure are important for reaction selectivity. Examples of such processes include catalytic cracking, alkylation, dealkylation, dehydrogenation, disproportionation, and transalkylation reactions. The coated zeolite catalysts of the present invention also find application in other hydrocarbon conversion processes in which carbon containing compounds are changed to different carbon containing compounds. Examples of such processes include hydrocracking, isomerization, dewaxing, oligomerization, and reforming processes.

DETAILED DESCRIPTION OF THE INVENTION

The coated zeolite catalyst of the present invention will contain a coating of second crystals of a second zeolite having an average particle size that is smaller than the average particle size of the first crystals and which second crystals cover at least a portion of the external surface of the first crystals. The second crystals can grow together and can form an overgrowth over the first crystals. By coating the first crystals with the second crystals, the accessibility of reactants and products to the external surface acid sites of the first zeolite is reduced.

The term "coating" as used in the specification and claims, means that a discontinuous layer of second zeolite crystals formed such as by being deposited or grown on and covering at least a portion of the external surface of the first zeolite crystals and having an average particle size that is less than the average particle size of the first crystals such that the second zeolite crystals are non-continuous with the first crystals, i.e., the crystalline framework of the second zeolite crystals is not part of or a continuation of the framework of the first zeolite. Hence, the layer deposited on the first zeolite crystals is not isocrystalline with the first zeolite crystals.

The average particle size of the second crystals will usually be substantially less than the average particle size of first crystals, e.g., at least 50% less than the average particle size of the first crystals. In addition, the second crystals will usually not be in crystallographic alignment with each other. Furthermore, the second crystals will usually not be disposed concentrically or follow the same longitudinal axis. Still further, the second zeolite crystals are usually not uniformly deposited on the first crystals.

Since the first crystals are larger than the second crystals, these crystals are sometimes referred to in the specification and claims as core crystals. The structure type of the first zeolite will depend upon the particular hydrocarbon process in which the coated zeolite catalyst is used. For instance, if the intended use of the coated zeolite catalyst is for selective toluene disproportionation, the first zeolite is preferably an intermediate pore size zeolite such as a zeolite having an MFI or MEL structure type. In addition, the core crystals can also comprise more than one zeolite. For example, the core crystals can comprise two or more zeolites having different structure types, different compositions, or combinations thereof. The core crystals will preferably have an average particle size of from about 0.1 to about 15 microns. In some applications, the average particle size will preferably be from about 1 to about 6 microns. In other applications such as the cracking of hydrocarbons, the preferred average particle size will be from about 0.1 to about 3 microns.

The amount of core crystals present in the coated catalyst will generally be an amount in the range of from about 10 weight percent to about 90 weight percent based on the total weight of zeolite present in the coated catalyst. The amount of core crystals present in the coated zeolite catalyst will usually be determined by the process in which the catalyst is used.

The second crystals, which are sometimes referred to in the specification and claims as coating crystals, will form a coating on at least a portion of the external surface of the core crystals. Preferably, the coating will cover at least 50 percent of the outer surface of the first crystals and more preferably will cover at least 75 percent of the external surface of the first crystals. In some applications it may be desirable for the coating to reduce accessibility of reactants to the acid sites on the external surface of the first zeolite by covering at least 50 percent, even more preferably at least 75 percent, and most preferably at least 90 percent of the acid sites. The coating will usually be non-uniform and may adhere to the surface of the core crystals. The average particle size of the coating crystals will be smaller than the average particle size of the core crystals. Preferably, the coating crystals will have an average particle size of less than 1 micron, more preferably from about 0.1 to about 0.5 micron. The structure type of the zeolite used to coat the core crystals will depend upon the particular hydrocarbon process in which the coated zeolite catalyst is used. For instance, if the intended use of the coated zeolite catalyst is for toluene disproportionation and the core crystals are an intermediate pore size zeolite having an MFI or MEL structure type, the coating crystals could comprise an intermediate pore size zeolite having less acidity than the core crystals. The coating crystals can also comprise more than one zeolite. For example, the coating crystals can comprise two or more zeolites having different structure types, different compositions, or combinations thereof.

The coated zeolite catalyst may be incorporated with a binder material resistant to the temperature and other conditions employed in hydrocarbon conversion processes such as metal oxides. The binder can be incorporated with the catalyst by mixing the binder with the catalyst and then forming the mixture into the appropriate catalyst shape. Examples of suitable binder materials include non-zeolitic material such as synthetic or naturally occurring substances such as clays, silicas, and/or metal oxides. Well known materials include silica, alumina, silica-alumina, magnesia, silica-magnesia, zirconia, silica-zirconia, silica-thoria, silica-beryllia, titania, silica-titania, ternary compositions, such as silica-alumina-thoria, silica-alumina-zirconia, silica-alumina-magnesia and silica-magnesia-zirconia, alumina sols, hydrated alumina, and clays such as bentonite or kaolin. The binder is usually present in an amount of from about 5 to about 95 weight percent and preferably about 15 to about 85 weight percent, based on the weight of the catalyst.

The term "average particle size" as used herein, means the arithmetic average of the diameter distribution of the crystals on a volume basis. The "diameter" of the crystals will be the sum of the length and diameters of crystals divided by 2.

The terms "acidity", "lower acidity" and "higher acidity" as applied to zeolite are known to persons skilled in the art. The acidic properties of zeolite are well known. However, with respect to the present invention, a distinction must be made between acid strength and acid site density. Acid sites of a zeolite can be a Bronsted acid or a Lewis acid. The density of the acid sites is important in determining the acidity of the zeolite. Factors directly influencing the acid strength are (i) the chemical composition of the zeolite framework, i.e., relative concentration and type of tetrahedral atoms, (ii) the concentration of the extra-framework cations and the resulting extra-framework species, (iii) the local structure of the zeolite, e.g., the pore size and the location, within the crystal or at/near the surface of the zeolite, and (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia absorption.

Zeolites suitable for use as the first zeolite and second zeolite include any of the naturally occurring or synthetic crystalline zeolites. Examples of these zeolites include large pore zeolites, medium pore zeolites, and small pore zeolites. These zeolites and their isotypes are described in "Atlas of Zeolite Structure Types", eds. W. H. Meier, D. H. Olson and Ch. Baerlocher, Elsevier, Fourth Edition, 1996, which is hereby incorporated by reference. A large pore zeolite generally has a pore size of at least about 7 Å and includes LTL, VFI, MAZ, MEI, FAU, EMT, OFF, *BEA, and MOR structure type zeolites (IUPAC Commission of Zeolite Nomenclature). Examples of large pore zeolites, include mazzite, offretite, zeolite L, VPI-5, zeolite Y, zeolite X, omega, Beta, ZSM-3, ZSM-4, ZSM-18, ZSM-20, SAPO-37, and MCM-22. An intermediate pore size zeolite generally has a pore size from about 5 Å to about 7 Å and includes, for example, ZSM-48 type and MFI, MEL, MTW, EUO, MTT, HEU, FER, MFS, TON structure type zeolites (IUPAC Commission of Zeolite Nomenclature). Examples of intermediate pore size zeolites include ZSM-5, ZSM-12, ZSM-22, ZSM-23, ZSM-34, ZSM-35, ZSM-38, ZSM-48, ZSM-50, ZSM-57, silicalite, and silicalite 2. A small pore size zeolite has a pore size from about 3 Å to about 5.0 Å and includes, for example, CHA, ERI, KFI, LEV, and LTA structure type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, erionite, chabazite, zeolite T, gmelinite, ALPO-17, and clinoptilolite.

In general, the chemical formula of anhydrous crystalline metallosilicate can be expressed in terms of moles as represented by the formula: $M_{2/n}O:W_2O_3:ZSiO_2$, wherein M is selected from the group consisting of hydrogen, hydrogen precursors, monovalent, divalent and trivalent cations and mixtures thereof; n is the valence of the cation and Z is a number of at least 2, preferably at least 3, said value being dependent upon the particular type of zeolite, and W is a metal in the anionic framework structure of the zeolite such as aluminum, gallium, boron, iron, titanium, or mixtures thereof.

Generally, the first and second zeolites of the coated zeolite catalyst comprise compositions having the following molar relationship:

$$X_2O_3::(n)YO_2,$$

wherein X is a trivalent element, such as titanium, boron, aluminum, iron, and/or gallium, Y is a tetravalent element such as silicon, tin, and/or germanium, and n has a value of at least 1, said value being dependent upon the particular type of zeolite and the trivalent element present in the zeolite.

When the first zeolite has an intermediate pore size, the zeolite preferably comprises a composition having the following molar relationship:

$$X_2O_3::(n)YO_2,$$

wherein X is a trivalent element, such as aluminum, gallium, iron, boron, titanium, or mixtures thereof Y is a tetravalent element such as silicon, tin, and/or germanium; and n has a value greater than 10, usually from about 20 to less than 20,000, more usually from 50 to 2,000, said value being dependent upon the particular type of zeolite and the trivalent element present in the zeolite.

As known to persons skilled in the art, the acidity of a zeolite can be reduced using many techniques. In addition, the acidity of a zeolite is dependent upon the form of the zeolite with the hydrogen form having the highest acidity and other forms of the zeolite such as the sodium form having less acidity than the acid form. Accordingly, the mole ratios of silica to alumina and silica to gallia disclosed in the specification and claims includes not only zeolites having the disclosed mole ratios, but also includes zeolites not having the disclosed mole ratios but having equivalent catalytic activity.

When the first zeolite is a gallosilicate intermediate pore size zeolite, the zeolite preferably comprises a composition having the following molar relationship:

$$Ga_2O_3:ySiO_2$$

wherein y is between about 20 and about 500, typically from 20 to 200. The zeolite framework may contain only gallium and silicon atoms or may also contain a combination of gallium, aluminum, and silicon.

When the first zeolite used in the coated zeolite catalyst is an aluminosilicate zeolite, the silica to alumina mole ratio will usually depend upon the structure type of the zeolite and the particular hydrocarbon process in which the catalyst is utilized and is therefore not limited to any particular ratio. Generally, however, and depending on the structure type of the zeolite, the zeolite will have a silica to alumina mole ratio of at least 2:1 and in some instances from 4:1 to about 7:1. For a number of zeolites, especially intermediate pore size zeolites, the silica to alumina mole ratio will be in the range of from about 10:1 to about 1,000:1. When the catalyst is utilized in acid catalyzed reactions such as cracking, the manufacture of paraxylene and benzene by the disproportionation of toluene, the alkylation of benzene or the like, the zeolite will be acidic and will preferably, when it is an intermediate pore size zeolite, have higher silica to alumina mole ratios, e.g., 20:1 to about 200:1.

As previously stated, the structure type of the first zeolite will depend on the particular hydrocarbon process in which the coated zeolite catalyst is utilized. For instance, if the coated zeolite catalyst is used for the reforming of naphtha to aromatics, the zeolite type of the first zeolite will preferably be LTL (example Zeolite L) and have a silica to alumina ratio from 4:1 to about 7:1. If the coated zeolite catalyst is used for xylene isomerization or the manufacture of paraxylene and benzene by the disproportionation of toluene, the first zeolite will preferably be an intermediate pore size zeolite, such as a MFI structure type (example ZSM-5). If the coated zeolite catalyst is to be used for cracking paraffins, the preferred pore size and structure type will depend on the size of the molecules to be cracked and the desired product. The selection of the first zeolite structure type for hydrocarbon conversion processes is known to persons skilled in the art.

The preferred structure type of the second zeolite will depend on the structure type of the first zeolite and the particular hydrocarbon process in which the coated zeolite catalyst is utilized. For instance, if the coated zeolite catalyst is used for xylene isomerization or the manufacture of paraxylene and benzene by the disproportionation of toluene, and the first zeolite is an intermediate pore size zeolite, such as a zeolite having a MFI structure type (example ZSM-5), the second zeolite will preferably be a low acidity intermediate pore size zeolite such as a MFI or MEL structure type zeolite. If the coated zeolite catalyst is to be used for cracking paraffins, the preferred pore size and structure type of the second zeolite will depend on the size of the molecules to be cracked and the desired product.

When the second zeolite is aluminosilicate zeolite, the silica to alumina mole ratio of the second zeolite, will usually depend upon the structure type of the first zeolite and particular hydrocarbon process in which the catalyst is utilized and is therefore not limited to any particular ratio. Generally, however, and depending on the structure type of the zeolite, the silica to alumina ratio will be at least 2:1. In applications where the aluminosilicate zeolite is an intermediate pore size zeolite and low acidity is desired, the second zeolite preferably has a silica to alumina mole ratio greater than the silica to alumina mole ratio of the first zeolite, and more preferably is greater than 200:1. The second zeolite can also have higher silica to alumina mole ratios, e.g., 300:1, 500:1, 1,000:1, etc. In certain applications, the second zeolite can be a Silicalite i.e., the second zeolite is a MFI structure type substantially free of alumina or Silicalite 2, i.e., the second zeolite is a MEL structure type substantially free of alumina. The pore size of the second zeolite will usually be a pore size that does not adversely restrict access of the desired molecules of the hydrocarbon feedstream to the catalytic phase of the first zeolite. For instance, when the materials of the feedstream which are to be converted by the first zeolite have a size from 5 Å to 6.8 Å, the second zeolite will preferably be a large pore zeolite or an intermediate pore size zeolite. However, the pore size of the second zeolite may be smaller than the materials in the feed stream and in some instances this may even be desirable. In these instances, access to the first zeolite crystals is through the macro porosity of the coated catalyst.

The coated zeolite catalysts are preferably prepared by converting a silica coating on the core crystals to the second zeolite coating crystals. This procedure involves first synthesizing the core crystals of the first zeolite. Processes for preparing the first zeolite are known to persons skilled in the art. For example, aluminosilicate MFI structure type zeolites can be made using the procedure described in U.S. Pat. No. 3,702,886.

Next, a silica-bound zeolite can be prepared by mixing a mixture comprising the core crystals, a silica gel or sol, water, and optionally an extrusion aid until a homogeneous composition in the form of an extrudable paste develops. The silica used in preparing the silica bound zeolite aggregate is preferably a silica sol and can contain various amounts of trivalent metal oxides such as alumina. The amount of zeolite in the dried extrudate at this stage will preferably range from about 20 to 90% by weight, more preferably from about 50 to 80% by weight, with the balance being primarily silica, e.g. about 20 to 50% by weight silica.

The resulting paste can then molded, e.g., extruded, and cut into small strands, e.g., 2 mm diameter extrudates, which are dried at 100–150° C. for a period of 4–12 hours and then calcined in air at a temperature of from about 400° C. to 550° C. for a period of from about 1 to 10 hours.

Optionally, the silica-bound aggregate can be made into a very small particles which have application in fluid bed processes such as catalytic cracking. This preferably involves mixing the zeolite with a silica containing matrix solution so that an aqueous solution of zeolite and silica binder is formed which can be sprayed dried to result in small fluidizable silica-bound aggregate particles. Procedures for preparing such aggregate particles are known to persons skilled in the art. An example of such a procedure is described by Scherzer (Octane-Enhancing Zeolitic FCC Catalysts, Julius Scherzer, Marcel Dekker, Inc. New York, 1990). The fluidizable silica-bound aggregate particles, like the silica bound extrudates described above, would then undergo the final step described below to convert the silica binder to a second zeolite.

Next, the silica present in the silica-bound zeolite is converted to a second zeolite. The silica of the silica bound zeolite can be converted to the second zeolite coating crystals by first aging the silica bound zeolite in an appropriate aqueous, solution at elevated temperature. Next, the contents of the solution and the temperature at which the aggregate is aged are selected to convert the amorphous silica binder into the desired second zeolite. The newly-formed second zeolite is produced as crystals on the first zeolite. After formation of the crystals, the resulting aggregate can be broken apart such as by crushing, to form the coated zeolite. Alternatively, the silica bound zeolite aggregate can be broken apart prior to conversion of the silica to the second zeolite. The second crystals can grow together and can even form an over-growth on the first crystals. The coated zeolite catalyst may consist essentially of the first crystals of the first zeolite and second crystals of the second zeolite.

After forming the coated zeolite, one or more additional coatings of smaller size second zeolite crystals can also be applied to the coated zeolite using, for example, the procedure described above. These zeolite coating crystals can be a structure type, composition, or combinations thereof, that are different from the first zeolite or second zeolite. The coated zeolite with the additional coating can be bound by the binder materials previously described.

The coated zeolite may be further ion exchanged as is known in the art either to replace at least in part the original metals present in the zeolite with a different cation, e.g. a Group IB to VIII of the Periodic Table metal such as nickel, copper, zinc, calcium or rare earth metals, or to provide a more acidic form of the zeolite by exchange of alkali metal with intermediate ammonium cation followed by calcination of the ammonium form to provide the acidic hydrogen form. The acidic form may be readily prepared by ion exchange using a suitable reagent such as ammonium nitrate solution followed by calcination to remove ammonia and form the acidic hydrogen form. Ion exchange is preferably conducted after formation of the coated zeolite catalyst. Particularly preferred cations are those which render the material catalytically active, especially for certain hydrocarbon conversion reactions. These include hydrogen, rare earth metals, and one or more metals of Groups IIA, IIIA, IVA, VA, VIA, VIIA, VIII, IB, IIB, IIIB, IVB, and VB of the Periodic Table of the Elements. Examples of suitable metals include Group VIII metals (i.e., Pt. Pd, Ir, Rh, Os, Ru, Ni, Co and Fe), Group IVA metals (i.e., Sn and Pb), Group VB metals (i.e., Sb and Bi), and Group VIIB metals (i.e., Mn, Tc and Re). Noble metals (i.e., Pt, Pd, Ir, Rh, Os and Ru) are sometimes preferred. Reference to the metals is intended to encompass such metal or metals in the elemental state (i.e., zero valence) or some other catalytically active form such as an oxide, sulfide, halide, carboxylate, and the like.

The coated zeolite catalyst of the present invention can be used in processing hydrocarbon feedstocks. Hydrocarbon feed-stocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbon feed is to undergo, the feed can contain metal or can be free of metals. Also, the feed can also have high or low nitrogen or sulfur impurities.

The conversion of hydrocarbon feeds can take place in any convenient mode, for example, in a fluidized bed, moving bed, or fixed bed reactors depending on the types of process desired.

The coated zeolite catalyst of the present invention by itself or in combination with one or more catalytically active substances can be used as a catalyst or support for a variety of organic, e.g., hydrocarbon compound, conversion processes. Examples of such conversion processes include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst feed rate) from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100 $hr^{-1}$.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 100 $hr^{-1}$ and an aromatic hydrocarbon/polyalkylaromatic hydrocarbon mole ratio of from about 1/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1. The resulting product from the reaction are long chain alkyl aromatics which when subsequently sulfonated have particular application as synthetic detergents;

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

(I) The hydrocracking of heavy petroleum feedstocks, cyclic stocks, and other hydrocrack charge stocks. The zeolite catalyst will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 to about 800 psig, a WHSV -olefin from about 0.4 $hr^{-1}$ to about 0.8 $hr^{-1}$, a WHSV -reformate of from about 1 $hr^{-1}$ to about 2 $hr^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 $hr^{-1}$ to about 10 $hr^{-1}$.

(M) The conversion of light paraffins to olefins and/or aromatics. Typical reaction conditions include temperatures from about 425° C. to about 760° C. and pressures from about 10 to about 2000 psig.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals processing steps. The first stage would be the coated zeolite catalyst comprising one or more catalytically active substances, e.g., a Group VIII metal, and the effluent from the first stage would be reacted in a second stage using a second zeolite, e.g., zeolite Beta, comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(P) A combination hydrocracking/dewaxing process in the presence of the coated zeolite catalyst comprising a hydrogenation component and a zeolite such as zeolite Beta. Typical reaction conditions include temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 $hr^{-1}$ to about 200 $hr^{-1}$ and an alcohol to olefin molar feed ratio from about 0.1/1 to about 5/1.

(R) The disproportionation of aromatics, e.g., the disproportionation toluene to make benzene and paraxylene. Typical reaction conditions include a temperature of from about 200° C. to about 760° C., a pressure of from about atmospheric to about 60 atmosphere (bar), and a WHSV of from about 0.1 hr$^{-1}$ to about 30 hr$^{-1}$.

(S) The conversion of naphtha (e.g., $C_6$–$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the coated zeolite at a temperature in the range of from about 400° C. to 600° C., preferably 480° C. to 550° C. at pressures ranging from atmospheric to 40 bar, and liquid hourly space velocities (LHSV) ranging from 0.1 to 15.

(T) The adsorption of alkyl aromatic compounds for the purpose of separating various isomers of the compounds.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100.

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with the coated zeolite catalyst at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the coated zeolite catalyst. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, the, catalytic conversion conditions over the coated zeolite catalyst include a temperature of from about 100° C. to about 760° C., a pressure of from about 0.1 atmosphere (bar) to about 200 atmospheres (bar), a weight hourly space velocity of from about 0.08 hr$^{-1}$ to about 2,000 hr$^{-1}$.

Although many hydrocarbon conversion processes prefer that the second zeolite crystals have lower acidity to reduce undesirable reactions external to the first zeolite crystals, some processes may prefer that the second crystals have higher acidity, e.g., cracking reactions.

Processes that also find particular application using the coated zeolite catalyst of the present invention are those where two or more reactions are taking place within the coated zeolite catalyst. This catalyst would comprise two different zeolites that are each separately tailored to promote or inhibit different reactions. A process using such a catalyst benefits not only from reduced non-selective surface acidity, but from a tailored catalyst.

Examples of preferred coated zeolite catalysts include the following:

1. A coated zeolite catalyst comprising an acidic second zeolite having cracking activity and an acidic first zeolite having acidic activity which is less than the acidic activity of the second zeolite and a smaller pore size than the second zeolite. The coated zeolite catalyst finds application in cracking larger size molecules and isomerizing the smaller cracked molecules. Examples of suitable second zeolites include Beta, Mordenite and the like. Examples of suitable first zeolites are ZSM-5, ZK-5, ZSM-11 and the like.

2. A coated zeolite catalyst comprising an acidic first zeolite having a large or intermediate pore size zeolite with cracking activity and an acidic second zeolite having smaller pore size than the second zeolite and having cracking activity. An example of a suitable first zeolite is ZSM-5 and an example of a suitable second zeolite is ZK-5. The coated zeolite catalyst finds particular application in cracking larger size molecules and further cracking the smaller cracked molecules to produce ethylene.

3. A coated zeolite catalyst comprising one zeolite (either the first or second zeolite) that has reduced acid activity and optionally contains a hydrogenation/dehydrogenation metal and another zeolite which has medium strength acidic activity and optionally a hydrogenation/dehydrogenation metal. The pore size of the zeolites will depend upon the type of process in which the catalyst is utilized. For example, the catalyst can be utilized in a combined xylene isomerization/ethylbenzene dealkylation process wherein the ethylbenzene is dealkylated to benzene and ethylene and isomers of xylenes are isomerized to equilibrium amounts. For use in such a process, the first zeolite will preferably be a large or intermediate pore size zeolite and the second zeolite will also preferably be a large or intermediate pore size zeolite.

4. A coated zeolite catalyst comprising a first acidic zeolite and a second zeolite which has little or no acidic activity. The pore size of the zeolites will depend on the type of process in which the catalyst is utilized. For example, if the catalyst is to be used in the disproportionation of aromatics, e.g., manufacture of benzene and paraxylene by the disproportionation of toluene, the first zeolite will preferably have an intermediate pore size and have acid activity and the second zeolite can be selected to control accessibility of reactants or products exiting the pores of the zeolite to the acid sites on the external surfaces of the first zeolite.

The coated zeolite catalyst of the present invention has particular application in the vapor phase disproportionation of toluene. Such vapor phase disproportionation comprises contacting toluene under disproportionation conditions with the coated zeolite catalyst to yield a product mixture which comprises a mixture of unreacted (unconverted) toluene, benzene and xylene. In the more preferred embodiment, the coated zeolite catalyst is first selectivated prior to use in the disproportionation process to enhance conversion of toluene to xylene and to maximize the catalyst selectivity towards the production of paraxylene. Processes for selectivating the catalyst are known to persons skilled in the art. For instance, selectivation can be accomplished by treating the surface of the catalyst with compounds of phosphorous and/or metal oxides such as magnesium, antimony, and manganese.

Selectivation may be also accomplished by exposing the catalyst in a reactor bed to a thermally decomposable organic compound, e.g., toluene, at a temperature in excess of the decomposition temperature of said compound, e.g. from about 480° C. to about 650° C., more preferably 540° C. to about 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0–10 moles of nitrogen or another inert gas per mole of organic compound. This process is conducted for a period of time until a sufficient quantity of coke has been deposited on the catalyst surface, generally at least about 2% by weight and more preferably from about 8 to about 40% by weight of coke. In a preferred embodiment, such a selectivation process is conducted in the presence of hydrogen in order to prevent rampant formation of coke on the catalyst.

Selectivation of the catalyst can also be accomplished by treating the catalyst with a selectivation agent such as an organosilicon compound. Examples of organosilicon compounds include polysiloxane including silicones, a siloxane, and a silane including disilanes and alkoxysilanes.

Silicone compounds that find particular application can be represented by the formula:

wherein $R_1$ is hydrogen, fluoride, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between 80 and 20,000 and preferably 150 to 10,000. Representative silicone compounds included dimethylsilicone, diethylsilicone, phenylmethylsilicone, methyl hydrogensilicone, ethylhydrogensilicone, phenylhydrogensilicone, methylethylsilicone, phenylethylsilicone, diphenylsilicone, methyltri fluoropropylsilicone, ethyltrifluoropropylsilicone, tetrachlorophenyl methyl silicone, tetrachlorophenylethyl silicone, tetrachloro phenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclotrisiloxane, octaethylcyclo tetrasiloxane, hexaphenylcyclotrisiloxane and octaphenylcyclo tetrasiloxane.

Useful silanes, disilanes, or alkoxysilanes include organic substituted silanes having the general formula:

wherein R is a reactive group such as hydrogen, alkoxy, halogen, carboxy, amino, acetamide, trialkylsilyoxy $R_1$, $R_2$ and $R_3$ can be the same as R or can be an organic radical which may include alkyl of from 1 to 40 carbon atoms, alkyl or aryl carboxylic acid wherein the organic portion of the alkyl contains 1 to 30 carbon atoms and the aryl group contains 6 to 24 carbon which may be further substituted, alkylaryl and arylalkyl groups containing 7 to 30 carbon atoms. Preferably, the alkyl group for an alkyl silane is between 1 and 4 carbon atoms in chain length.

When used the vapor phase disproportionation of toluene, the catalyst preferably comprises MFI-type zeolite core crystals having an average particle size from about 2 to about 6 microns, a silica to alumina mole ratio of from about 20 to about 200:1, preferably, 25:1 to about 120:1, and second crystals having a MFI or MEL structure type and an average particle size of less than about 0.5 micron, and more preferably less than 0.1 micron having a alumina to silica mole ratio in excess of about 200:1 to about 10,000:1 and most preferably greater than 500:1.

Once the catalyst has been selectivated to the desired degree, reactor selectivation conditions are changed to disproportionation conditions. Disproportionation conditions include a temperature between about 400° C. and 600° C., more preferably between about 425° C. and 510° C., at a hydrogen to toluene mole ratio of from 0 to about 10, preferably between about 0.1 and 5 and more preferably from about 0.1 to 1, at a pressure between about 1 atmosphere and 100 atmospheres and utilizing WHSV of between about 0.5 and 50

The coated zeolite catalyst of the present invention also finds particular application as a catalyst in a process for isomerizing one or more xylene isomers in a $C_8$ aromatic feed to obtain ortho-, meta-, and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. Ethylbenzene in the feed is either removed from the stream or is converted during the process to xylenes or to benzene which are easily separated by distillation. The isomerate is blended with fresh feed and the combined stream is distilled to remove heavy and light by-products. The resulting $C_8$ aromatics stream is then recycled to the separation device to repeat the cycle.

It is important that xylene isomerization catalysts produce a near equilibrium mixture of xylenes and it is also desirable that the catalyst convert ethylbenzene with very little net loss of xylenes. The coated zeolite catalyst finds particular application in this regard. The silica to alumina mole ratios of the first zeolite and second zeolite can be selected to balance xylene isomerization and ethylbenzene dealkylation while minimizing undesirable side reactions. When used for xylene isomerization, the first zeolite will usually be an aluminosilicate zeolite having a silica to alumina mole ratio from 70:1 to about 700: or a gallosilicate having a silica to gallia mole ratio from about 24:1 to about 500:1 and the second zeolite will usually be aluminosilicate zeolite having a silica to alumina mole ratio greater than 200:1 or a gallosilicate having a silica to gallia mole ratio greater than 100:1. If the feed stream also contains ethylbenzene, the coated catalyst will also usually contain one or more metals such as platinum. The process is carried out by contacting a $C_8$ aromatic stream containing one or more xylene isomers, ethylbenzene, or mixtures thereof, under isomerization conditions with the coated zeolite catalyst. Preferably, at least 30% of the ethylbenzene is converted.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 3.0 to 30.0 moles of hydrogen per mole of alkylbenzene. If hydrogen is used, the metal components of the catalyst preferably include 0.1 to 2.0 wt. % of a hydrogenation/dehydrogenation component selected from Group VIII of the Periodic Table of Elements, especially platinum, palladium, or nickel. By Group VIII metal component, it is meant the metals and as well as their compounds such as oxides and sulfides.

The coated zeolite catalysts of the present invention are especially useful as a catalyst in a process for cracking a naphtha feed, e.g., $C_4^+$ naphtha feed, particularly a $C_4^-$ 290° C. naphtha feed to produce low molecular weight olefins, e.g., $C_2$ through $C_4$ olefins, particularly ethylene and propylene. Such a process is preferably carried out by contacting the naphtha feed at temperatures ranging from 500° C. to about 750° C., more preferably 550° C. to 675° C., at a pressure from subatmospheric up to 10 atmospheres, but preferably from about 1 atmosphere to about 3 atmospheres.

The coated zeolite catalysts of the present invention are especially useful as a catalyst in the transalkylation of polyalkylaromatic hydrocarbons. Examples of suitable polyalkylaromatic hydrocarbons include di-, tri-, and tetra-alkyl aromatic hydrocarbons, such as diethylbenzene, triethylbenzene, diethylmethylbenzene (diethyl-toluene), diisopropyl-benzene, triisopropylbenzene, diisopropyltoluene, dibutylbenzene, and the like. Preferred polyalkylaromatic hydro-carbons are the dialkyl benzenes. Particularly preferred polyalkyl-aromatic hydrocarbons are diisopropylbenzene and diethylbenzene.

The transalkylation process will preferably have a molar ratio of aromatic hydrocarbon to polyalkylaromatic hydrocarbon of preferably from about 0.5:1 to about 50:1, and more preferably from about 2:1 to about 20:1. The reaction temperature will preferably range from about 340° C. to 500° C., and the pressure will be preferably in the range of about 50 psig to 1,000 psig, preferably 300 psig to 600 psig. The weight hourly space velocity will range from about 0.1 to 10.

The coated zeolite catalysts find particular application in processes for converting aromatic compounds from paraffins or olefins. Example of suitable paraffins or olefins including aliphatic hydrocarbons containing 2 to 12 carbon atoms. The hydrocarbons may be straight chain, open or cyclic and may be saturated or unsaturated. Example of hydrocarbons include ethane, ethylene, propane, propylene, n-butane, n-butenes, isobutane, isobutene, and straight- and branch-chain and cyclic pentanes, pentenes, hexanes, and hexenes.

The aromatization conditions include a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The coated zeolite catalyst used in the aromatization process preferably comprises core crystals of an intermediate pore size zeolite such a MFI type zeolite (example ZSM-5), and coating crystals of a intermediate pore size such as a MFI or MEL structure type. The catalyst preferably contains gallium. Gallium may be incorporated into the during synthesis of the catalyst or it may be exchanged or impregnated or otherwise incorporated into the zeolite after synthesis. Preferably 0.05 to 10 wt. percent, and most preferably 0.1 to 2.0 wt. percent gallium is associated with the coated zeolite catalyst. The gallium can be associated with the first zeolite, second zeolite, or both zeolites.

The coated zeolite catalyst also finds particular application in processes for the production of xylenes by catalytic methylation of toluene in the presence of the coated zeolite catalyst. In carrying out the methylation process, the catalyst and reactants can be heated to reaction temperature separately or together. Reaction temperatures are from about 300° C. to about 700° C. and preferably about 400° C. to about 700° C. The reaction is preferably carried out at a pressure from about 1 to 1000 psig, a weight hourly space velocity of between about 1 and about 2000, a molar ratio of methylating agent to toluene between about 0.05 and about 5 and a weight hourly space velocity of between about 1 and about 200 and preferably between about 5 and about 150 weight of charge per weight of catalyst per hour. The coated zeolite catalyst can be selectivated to improve its paraxylene selectivity. Selectivation can be accomplished by the techniques used to enhance its paraxylene selectivity for use in the disproportionation of toluene.

Typical methylating agents include methanol, dimethylether, methylchloride, methylbromide and dimethylsulfide. One skilled in the art will know that other methylating agents may be employed in the process of this invention based on the description provided therein. Preferred methylating agents are methanol and dimethylether. Methanol is most preferred.

The methylation process can be carried out as a batch type, semi-continuous or continuous operation utilizing a fixed or moving bed catalyst system. Multiple injection of the methylating agent may be employed.

Toluene and the methylating agent are usually premixed and fed together into the reaction vessel to maintain the desired ratio between them with no local concentration of either reactant to disrupt reaction kinetics. Individual feeds can be employed, however, if care is taken to insure good mixing of the reactant vapors in the reaction vessel. Instantaneous concentration of methylating agent can be kept low by staged additions thereof. By staged additions, toluene/methylating agent concentrations can be maintained at optimum levels to give good toluene conversions. Hydrogen gas can be supplied to the reaction as an anticoking agent and diluent.

The following examples illustrate the invention:

EXAMPLE 1

I. Catalyst A

Figure 1:
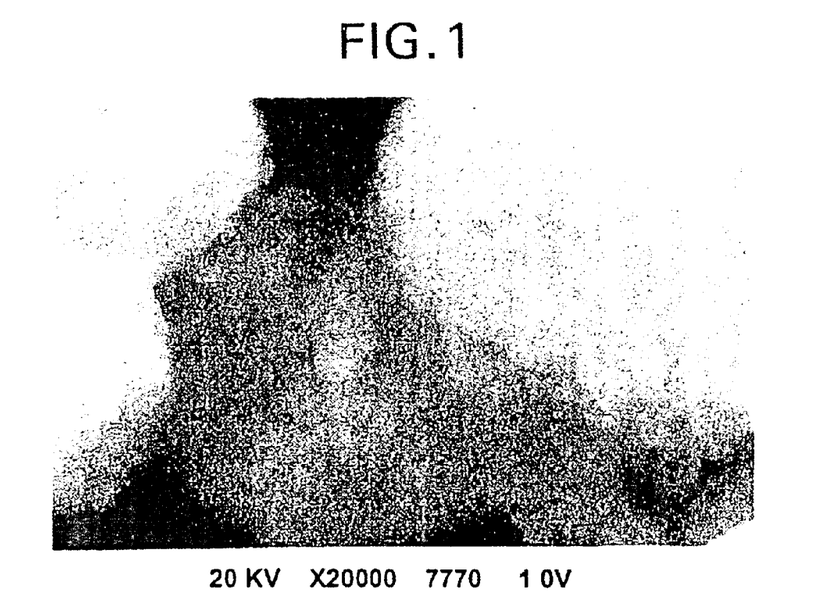
FIG. 1 is a SEM micrograph (20,000 times) of Catalyst A of Example 1

Catalyst A comprised 70 wt. % ZSM-5 core crystals (average particle size of 3.0 microns) having a silica to alumina mole ratio of about 66:1 and 30 wt. % silicalite coating crystals. The catalyst was prepared by first mixing the ZSM-5 core crystals with amorphous silica and then extruding the mixture into a silica bound extrudate. Next, the silica binder of the extrudate was converted to the second zeolite by aging the aggregate at elevated temperatures in an aqueous solution containing a template and hydroxy ions sufficient to covert the silica to the binder crystals. The resulting product was then washed, dried, calcined, ion exchanged into the hydrogen form, and crushed. FIG. 1 is a SEM micrograph of Catalyst A.

II. Catalyst B

Catalyst B comprised about 70 wt. % MFI structure type zeolite core crystals (average particle size of 3.0 microns) having a silica to gallia mole ratio of about 100:1, 30 wt. % MFI structure type binder crystals having a silica to gallia mole ratio of about 900:1, and about 0.49 wt. % platinum. The catalyst was prepared by first mixing the core crystals, platinum salt, and amorphous silica containing a trace amount of gallia and then extruding the mixture into a silica bound extrudate. Next, the silica binder of the extrudate was converted to the zeolite binder by aging the extrudate at elevated temperatures in an aqueous solution containing a template and hydroxy ions sufficient to covert the silica to the binder crystals. The resulting zeolite bound zeolite was then washed, dried, calcined, ion exchanged into the hydrogen form, and crushed.

III. Catalyst C

Catalyst C comprised zeolite Beta coated with ZSM-48. The catalyst was prepared by first forming silica bound extrudates containing zeolite beta (sodium form and a silica to alumina mole ratio of 12.4). The extrudates were formed as follows:

| Components Used For Preparation | Quantity (Grams) |
|---|---|
| Beta crystals | 300.00 |
| SiO$_2$ gel (Aerosil 300) | 11.5 |
| Silica sol (Nyacol 2034 DI) | 346.2 |
| Water | 70.7 |
| Extrusion Aid (Methocel) | 2.3 |

The components were mixed in the order listed. A plastic extrudable dough was obtained. The dough was extruded into approximately 2 mm extrudates. The extrudates were dried overnight at 120° C. and then calcined for 8 hours at 510° C.

Composition of the calcined silica-bound extrudate (on a dry basis):

Beta=70.0 wt. %

SiO$_2$=30 wt. %

The silica bound extrudates were converted to zeolite beta bound by ZSM-48 as follows:

| Components Used For Preparation | Quantity, (Grams) | Component No. |
|---|---|---|
| NaOH | 0.577 | 1 |
| 1,6 diammino hexane | 3.50 | 2 |
| Water | 22.52 | 3 |
| Rinse Water | 10.01 | 4 |
| Silica bound beta | 26.18 | 5 |

A solution comprising Components 1, 2, and 3 was prepared at room temperature and transferred to 100 ml autoclave. Component 4 was used to transfer the solution to the contents of the autoclave. The contents of the autoclave were stirred and finally 26.18 grams of beta crystals (saturated with 23.6 wt. % water) were added to the contents of the autoclave. The molar composition of the synthesis mixture was:

0.71 Na$_2$O/3 R/10SiO$_2$/217 H$_2$O

Crystallization was carried out by heating in 2 hours to 150° C. and then maintaining the temperature at 150° C. for 35 hours. The resulting product was washed with 400 ml of water. The conductivity of the last wash water was 25 µS/cm. The product was dried overnight at 120° C., calcined in air at 500° C. for 16 hours, and crushed to break apart the extrudate.

Figure 2:
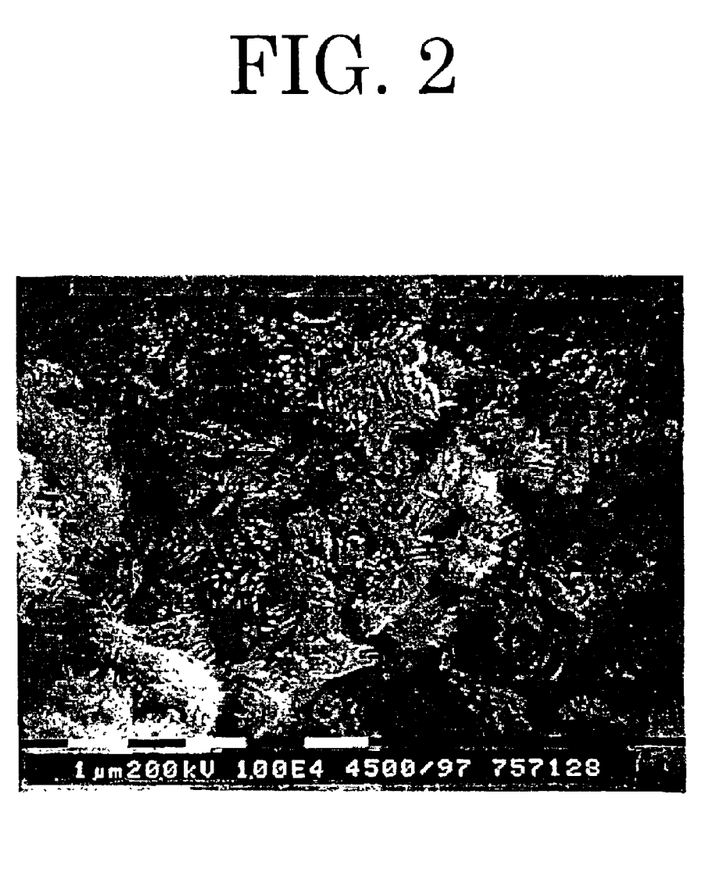
FIG. 2 is a SEM micrograph (10,000 times) of Catalyst C of Example 1

The product was analyzed by XRD and SEM with the following results:

| | |
|---|---|
| XRD: | Showed typical patterns for zeolite beta and ZSM-48 with excellent crystallinity. |
| SEM: | 10,000 times Micrograph (FIG. 2) shows the Beta crystals are coated with newly formed crystals having a submicron size. |
| | Core crystals = 70 wt. % |
| | Coating crystals = 30 wt. % |

Toluene methylation tests were carried out using Catalyst A, Catalyst B, and Catalyst C. An amount of 1.0 gram of each catalyst was loaded into a tubular reactor. The catalysts tested were in powdered form (<100 mesh). The results are shown in Table I. All performance data are the average of the run.

TABLE I

| | Catalyst A | Catalyst B | Catalyst C |
|---|---|---|---|
| Temp., ° C. | 551 | 449 | 350 |
| Pressure, psia | 17.9 | 16 | 365 |
| WHSV ($^g$feed/$^g$cat$^h$) | 20.6 | 10.6 | 7.6 |
| Time on Stream, hr | 17 | 4 | 22 |
| H$_2$/methanol/toluene (mole:mole:mole) | 1.5/0.33/1.0 | 0.47/0.17/1.00 | 0/0.11/1.00 |
| Product Distribution (wt. %)* | | | |
| C$_{6-}$ | 3.3 | 3.2 | ** |
| Benzene | 2.0 | 1.8 | 5.1 |
| Xylenes | 79.6 | 75.0 | 67.6 |
| EB | 0.1 | 0.1 | 0.2 |
| Trimethyl benzene | 0.1 | 0.3 | 6.8 |
| Methyl ethyl benzene | 9.9 | 7.3 | ** |
| C$_{7+}$and A$_{9+}$ (other) | 5.0 | 12.2 | 20.2 |
| | 100.0 | 99.9 | 99.9 |
| Performance Data | | | |
| Toluene Conv. % | 15.2 | 13.5 | 11.4 |
| MeOH Conv. % | 97.5 | 99.7 | 99.9 |
| p-Xylene in xylenes | 52.0 | 34.6 | 26.8 |

*Excluding water and unreacted feed
**Not determined

EXAMPLE 2

Preparation of platinum-containing zeolite coated MFI type gallium silicate catalyst.

MFI type gallosilicate crystals (4 micron size spherical crystals and SiO$_2$/Ga$_2$O$_3$=48) were formed into silica bound extrudates or follows:

| Components Used For Preparation: | Quantity (Grams) | Component No. |
|---|---|---|
| Silica Sol (Nalcoag 1034) | 49.44 | 1 |
| Silica gel (Aerosil 300) | 4.72 | 2 |
| H$_2$PtCl$_6$.6H$_2$O | 0.93 | 3 |

-continued

| Components Used For Preparation: | Quantity (Grams) | Component No. |
|---|---|---|
| Water | 11.07 | |
| Rinse Water | 3.27 | 4 |
| Gallium silicate MFI Crystals | 49.86 | 5 |
| Extrusion aid (hydroxypropyl methyl cellulose) | 0.34 | 6 |

The components were mixed in a dough mixer in the order indicated. After adding the extrusion aid, and mixing for about 15 minutes, a dough was obtained. The dough was divided into several portions and dried in an oven at 120° C. for 16 hours. The dried portions were crushed, and then calcined at 490° C. for 24 hours in air.

The silica coated core crystals were converted into zeolite bound zeolite as follows:

| Components Used For Preparation | Quantity (Grams) |
|---|---|
| Component A | |
| NaOH pellets (98.7%) | 1.162 |
| Water | 16.08 |
| Rinse Water (A) | 17.06 |
| Ga$_2$O$_3$ (99.995%) | 0.144 |
| Component B | |
| Tetrapropylammonium bromide | 7.96 |
| Water | 16.16 |
| Rinse Water (B) | 15.64 |
| Component C | |
| Silica coated gallosilicate MFI | 60.07 |

Component A was prepared by combining the ingredients and then boiling until a clear solution was obtained. The solution was cooled to room temperature and water loss due to boiling was corrected. Component B was prepared at room temperature. Component B was added to Component A using rinse water (2) to form D. Component C was added to a 300 ml stainless steel autoclave and D was added to the autoclave using rinse water (1).

The molar composition of the synthesis mixture was:

0.47/Na$_2$O/1.00TPABr/0.025Ga$_2$O$_3$/10SiO$_2$/150H$_2$O

The autoclave was heated from room temperature to 150° C. in 2 hours and maintained at this temperature for 40 hours. The resulting product was washed 5 times at 60° C. with 1800 ml of water. The conductivity of the last wash water was 50 µS/cm. The product was dried at 120° C., calcined in air at 500 for 12 hours, and crushed.

The product was analyzed by XRD and SEM with the following results:

| XRD: | Excellent crystallinity |
|---|---|
| SEM: | 5 micron size spherical crystals coated with coffin type crystals. No visible amorphous silica. The coating crystals had the following dimensions: 0.50–0.75 µm length, about 0.2 µm width, and about 0.4 thick. |

Simultaneous xylene isomerization and ethylbenzene reduction reactions were conducted using the coated catalyst as prepared above by passing an artificial feed through a fixed bed reactor. The feed contained C$_8$–C$_{10}$ nonaromatics (0.6%), toluene (1.3%), ethylbenzene (15.6%), p-xylene (1.4%), m-xylene (65.1%), o-xylene (16.0%) and A9+ (<0.1%). The catalyst was pretreated in H$_2$ for about 1 h at 775° F. and 250 psig. Subsequently, the feed was introduced into the reactor. After about 112 hours on stream, the run conditions were changed. A summary of the conditions and results are shown in Table II:

TABLE II

| | Condition No. | |
|---|---|---|
| | 1 | 2 |
| Temperature (° F.) | 775 | 792 |
| HC Inlet Partial Pressure (psi) | 118 | 76 |
| H$_2$ Inlet Partial Pressure (psi) | 118 | 151 |
| WHSV (#/#/Hr) | 10 | 10 |
| Hours On-Oil | 112 | 148 |
| % EB reacted | 72.3 | 73.9 |
| Ring Loss (% of feed aromatic rings) | 0.9 | 1.0 |
| Xylenes Loss (% of feed xylenes) | 4.5 | 3.6 |
| PX approach to equilibrium (%)* | 100.7 | 100.4 |

The percent, % EB reacted, was determined by the formula: % EB Conv=100×[EB in−EB out] divided by EB in; Aromatics ring loss % was determined by the formula: 100×(moles of aromatics in feed−moles of aromatics in product)/(moles of aromatics in feed). Loss of xylenes was determined by the formula: 100×(moles of xylenes in feed−moles of xylenes in product)/(moles of xylenes in feed) and PX approach to equilibrium was determined by the formula: (Product PX/Xs−Feed PX/Xs)/(Equilibrium PX/Xs−FeedPX/Xs)×100.

EXAMPLE 3

A coated zeolite catalyst was prepared which comprised about 70 wt. % ZSM-5 core crystals (average particle size of 3.0 microns) having a silica to alumina mole ratio of about 70:1 and 30 wt. % silicalite coating crystals. The catalyst was prepared by first mixing the ZSM-5 core crystals with amorphous silica and then extruding the mixture into a silica bound extrudate. Next, the silica binder of the extrudate was converted to the second zeolite by aging the aggregate at elevated temperatures in an aqueous solution containing a template and hydroxy ions sufficient to covert the silica to the binder crystals. The resulting product was then washed, dried, calcined, ion exchanged into the hydrogen form, and crushed. An additional coating of silicalite was applied to the zeolite coated product by first mixing the coated ZSM-5 core crystals with amorphous silica and then extruding the mixture into a silica bound extrudate. Next, the silica binder of the extrudate was converted to coating silicalite by aging the aggregate at elevated temperatures in an aqueous solution containing a template and hydroxy ions sufficient to covert the silica to the binder crystals. The resulting product was then washed, dried, calcined, ion exchanged into the hydrogen form, and crushed.

The zeolite coated zeolite was tested for the disproportionation of toluene. The catalyst was evaluated under 4 separate test conditions as shown in Table III below. On-oil catalyst performance for the catalyst is shown in Table IV.

TABLE III

On-Oil Conditions

| Feed = Toluene | Test 1 | Test 2 | Test 3 | Test 4 |
|---|---|---|---|---|
| Temperature (° F.) | 834 | 875 | 834 | 854 |
| Feed Part. Press (psi) | 94 | 94 | 94 | 94 |
| $H_2$ Part. Press (psi) | 187 | 187 | 187 | 187 |
| WHSV (#/#/#) | 3.0 | 3.0 | 2.1 | 2.1 |

TABLE IV

On-Oil Catalyst Performance

| | Test 1 | Test 2 | Test 3 | Test 4 |
|---|---|---|---|---|
| Conversion | 30.7 | 41.5 | 36.9 | 42.7 |
| % PX in MX + OX + PX | 24.3 | 24.3 | 24.2 | 24.2 |
| BZ | 12.6 | 17.2 | 15.1 | 17.8 |
| Xylene | 16.1 | 21.1 | 18.3 | 21.6 |
| $C_5^-$ | 0.4 | 0.9 | 0.6 | 1.0 |
| $A_9^+$ | 1.4 | 1.9 | 1.7 | 2.0 |
| EB | 0.1 | 0.3 | 0.2 | 0.4 |

The results show that the catalyst had good activity for toluene disproportionation.

EXAMPLE 4

Preparation of MFI Core Crystals coated with MFI Crystals

A zeolite coated zeolite was prepared which comprised ZSM-5 core crystals having a silica to alumina mole ratio of about 75 and a particle size of 3 microns which were coated with silicalite.

The catalyst was prepared by mixing the ZSM-5 core crystals with silica and then extruding the mixture to form a silica-bound extrudate. The extrudate was crushed, calcined, and dried. The product comprised ZSM-5 core crystals coated with silica. The silica coated core crystals were converted into MFI core crystals coated with silicalite as follows:

| Component | Ingredients | Quantity in Grams |
|---|---|---|
| 1 | NaOH (98.7%%) | 1.311 |
| | $H_2O$ | 25.09 |
| 2 | TPABr | 8.05 |
| | $H_2O$ | 24.95 |
| 3 | Silica coated MFI-crushed, calcined, dried | 59.77 |
| 4 | Rinse Water | 10.61 |
| 5 | Rinse Water | 29.38 |

Components 1 and 2 were prepared at room temperature. Component 2 was added to Component 1 using rinse water 5 to form A. Component 3 was transferred to a 300 ml stainless steel autoclave and then A was added to the contents of the autoclave using rinse water 4.

The synthesis liquor had the following molar composition:

The autoclave was heated to 150° C. in 2 hours and kept at 150° C. for 40 hours. The product was then washed 5 times with 1800 ml of water. The conductivity of the last wash water was less than 50 μS/cm. The product was dried at 120° C. and calcined at 500° C. for 12 hours.

| XRD: | MFI present and crystallinity good. |
|---|---|
| SEM: | Showed the presence of zeolite core crystals coated with small zeolite crystals that were partially intergrown. Some free crystals having a length of 0.5 μm were also present. |

A toluene methylation test was carried out using the catalyst as prepared above. An amount of approximately 1.0 gram of the catalyst in powdered form (40/60 mesh) was loaded into a tubular reactor. The results are shown in Table V.

TABLE V

| Temp., ° C. | 450 | 450 |
|---|---|---|
| Pressure, psia | 15 | 15 |
| WHSV ($^g$feed/$^g$cat$^h$) | 14 | 14 |
| Time on Stream, hr | 1 | 3 |
| methanol/toluene (mole/mole) | 0.99 | 0.99 |
| Product Yields* | | |
| Benzene | 7.0 | 2.4 |
| Xylene | 68.4 | 71.7 |
| Trimethyl benzene | 9.7 | 11.2 |
| Methyl ethyl benzene | 6.1 | 7.2 |
| Performance Data | | |
| Toluene Conv. % | 46.8 | 45.5 |
| MeOH Conv. % | 100.0 | 100.0 |
| p-Xylene in xylenes | 28.0 | 30.9 |

*Product Yield = moles formed/moles toluene reacted

EXAMPLE 5

Preparation of MFI core crystals coated with MEL crystals

A zeolite coated zeolite catalyst was prepared which comprised ZSM-5 core crystals having a silica to alumina mole ratio of about 75 and a particle size of about 3 microns which were coated with silicalite 2.

The coated catalyst was prepared by mixing the ZSM-5 core crystals with silica and then extruding the mixture to form a silica-bound extrudate. The extrudate was crushed, calcined, and dried. The product comprised ZSM-5 core crystals coated with silica. The silica coated core crystals were converted into zeolite coated zeolite as follows:

| Component | Ingredients | Quantity in Grams |
|---|---|---|
| 1 | NaOH (98.6%%) | 0.97 |
| | $H_2O$ | 22.78 |
| 2 | Tetrabutylammonium hydroxide | 7.65 |
| | $H_2O$ | 22.01 |
| 3 | Silica coated MFI-crushed, calcined, and dried | 54.63 |
| 4 | Rinse Water | 19.36 |

Components 1 and 2 were prepared at room temperature. Component 2 was added to Component 1 using rinse water 4 to form A. Component 3 was transferred to a 300 ml stainless steel autoclave and A was added to the contents of the autoclave.

The autoclave was heated to 150° C. in 2 hours and kept at 150° C. for 40 hours. The product was then washed 5 times with 1800 ml of water. The conductivity of the last wash water was less than 50 μS/cm. The product was dried at 120° C. and calcined at 500° C. for 12 hours.

SEM: Showed the prescence of zeolite core crystals coated with small zeolite crystals that were intergrown.

A toluene methylation test was carried out using the catalyst prepared as described above. An amount of approximately 1.0 gram of the catalyst in powdered form (40/60 mesh) was loaded into a tubular reactor. The results are shown in Table VI.

TABLE VI

| Temp., ° C. | 450 | 450 |
|---|---|---|
| Pressure, psia | 15 | 15 |
| WHSV ( g feed/g cat h) | 14 | 14 |
| Time on Stream, hr | 1 | 3 |
| Methanol/toluene (mole/mole) | 0.99 | 0.99 |
| Product Yields* | | |
| Benzene | 7.7 | 2.5 |
| Xylene | 72.0 | 78.5 |
| Trimethyl benzene | 7.6 | 8.6 |
| Methyl ethyl benzene | 6.6 | 6.6 |
| Performance Data | | |
| Toluene Conv. % | 40.8 | 37.1 |
| MeOH Conv. % | 100.0 | 100.0 |
| p-Xylene in xylenes | 31.8 | 33.4 |

*Product Yield = moles formed/moles toluene reacted

What is claimed is:

1. A coated zeolite catalyst, said coated zeolite catalyst being selected from the group consisting of:
   (I) A zeolite catalyst comprising:
      (a) first crystals of a first acidic zeolite having catalytic activity;
      (b) a discontinuous is layer of second crystals of a second zeolite having lees acidity than said first zeolite and a structure type that is the same as said first zeolite and said second crystals have an average particle size less than the average particle size of said first crystals covering at least a portion of the external surface of said first crystals; and
      (c) non-zeolitic binder present in an amount of at least about 15 weight percent based on the weight of the zeolite catalyst;
   (II) A zeolite catalyst comprising:
      (a) first crystals of a first acidic zeolite having catalytic activity; and,
      (b) a discontinuous layer of second crystals of a second zeolite and a third zeolite said second crystals having an average particle size less than the average particle size of said first crystals and covering at least a portion of the external surface of said first crystals, and said third zeolite has a structure type, composition, or both that is different from said second zeolite:
   (III) A zeolite catalyst comprising:
      (a) first crystals of a first acidic zeolite having catalytic activity;
      (b) a discontinuous layer of second crystals of a second zeolite having a structure type that is different from said first zeolite and said second crystals have an average particle size less than the average particle size of said first crystals covering at least a portion of the external surface of said first crystals;
      (c) non-zeolitic binder present in an amount of at least about 15 weight percent based on the weight of the zeolite catalyst; and,
   (IV) Mixtures thereof.

2. The coated catalyst recited in claim 1, wherein said second crystals cover at least 50 percent of the external surface of said first crystals.

3. The coated catalyst recited in claim 2, wherein said second crystals have an average particle size that is at least 50% less than the average particle of the second crystals.

4. The coated catalyst recited in claim 3 wherein said second crystals are grown together.

5. The coated catalyst recited in claim 4, wherein the accessibility of reactants to the external acid sites of the first zeolite is reduced by at least 75 percent.

6. The coated catalyst recited in claim 3 wherein said first crystals have an average particle size of from about 0.1 to about 15 microns.

7. The coated catalyst recited in claim 6, wherein said second crystals have an average particle size of less than 1 micron.

8. The coated catalyst recited in claim 7, wherein said first zeolite and said second zeolite are independently a structure type selected from the group consisting of OFF, BEA, MAZ, MEI, FAU, EMT, LTL, MOR, MFI, MFS, MEL, MTW, MTT FER, EUO, HEU, TON, CHA, ERI, KFI, LEV, and LTA.

9. The coated catalyst recited in claim 3 wherein said first zeolite and said second zeolite are intermediate pore size zeolites and each are independently a composition having the following molar relationship:

$$X_2O_3:(n)YO_2,$$

wherein X is aluminum, boron, iron, and/or gallium, Y is silicon, tin, and/or germanium, and n has a value greater than 10.

10. The coated catalyst recited in claim 9, wherein said second zeolite of (II), (III), or both has lower acidity than said first zeolite.

11. The coated catalyst recited in claim 1, wherein the acidity of said second zeolite of (II), (III), or both is higher than the acidity of said first zeolite.

12. The coated catalyst recited in claim 3, wherein said first zeolite and said second zeolite have a large pore size or an intermediate pore size.

13. The coated catalyst recited in claim 3, wherein said first zeolite and said second zeolite have an intermediate pore size or small pore size.

14. The coated catalyst recited in claim 8, wherein said first zeolite and said second zeolite are an aluminosilicate zeolite or a gallium silicate zeolite.

15. The coated catalyst recited in claim 14, wherein said second crystals are prepared by aging at elevated temperatures silica-coated first zeolite crystals in an aqueous ionic solution containing a source of hydroxy ions sufficient to convert the silica in the aggregate to the second zeolite.

16. The coated catalyst recited in claim 14, wherein said second zeolite has a silica to alumina mole ratio greater than about 200:1.

17. The coated catalyst recited in claim 16, wherein said first zeolite has a silica to alumina mole ratio of from about 20:1 to about 200:1.

18. The coated catalyst recited in claim 17, wherein said second zeolite has a silica to alumina mole ratio greater than 500:1.

19. The coated catalyst recited in claim 7, wherein first crystals of said first zeolite have an average particle size of from about 1 to about 6 microns.

20. The coated catalyst recited in claim 19, wherein said second crystals of said zeolite have an average particle size of from about 0.1 to about 0.5 micron.

21. The coated catalyst recited in claim 3, wherein the pore size of said first zeolite is larger than the pore size of said second zeolite.

22. The coated catalyst recited in claim 3, wherein the pore size of said second zeolite is larger than the pore size of said first zeolite.

23. The coated catalyst recited in claim 5, wherein said catalyst further comprises a catalytically active metal.

24. The coated catalyst recited in claim 1, wherein said zeolite catalyst of II further comprises a binder.

25. The coated catalyst recited in claim 24, wherein said binder of said zeolite catalyst of II comprises silica.

26. The coated catalyst recited in claim 1, wherein said first crystals comprise at least 75% by weight of said coated zeolite catalyst based on weight of said first zeolite and said second zeolite.

27. The coated catalyst recited in claim 1, wherein said coating further comprises at least one additional zeolite.

* * * * *